United States Patent

Hijiya et al.

Patent Number: 5,679,857
Date of Patent: Oct. 21, 1997

[54] METHOD OF PREPARING D-AMINO ACID-N-(S)-α-ALKYLBENZYLAMIDE

[75] Inventors: Toyoto Hijiya; Chiaki Mochizuki; Tadashi Takemoto, all of Kawasaki, Japan

[73] Assignee: Ajinomoto Co., Inc., Tokyo, Japan

[21] Appl. No.: 558,663

[22] Filed: Nov. 16, 1995

[30] Foreign Application Priority Data

Dec. 8, 1994 [JP] Japan ................................ 6-304783

[51] Int. Cl.$^6$ .................................................. C07C 231/18
[52] U.S. Cl. ........................... 564/304; 564/164; 564/165; 564/194; 564/196; 564/198; 564/424; 564/425
[58] Field of Search ................................ 564/303, 304, 564/164, 165, 198, 424, 425, 194, 196

[56] References Cited

U.S. PATENT DOCUMENTS 5,306,826  4/1994  Boesten ............................... 548/534

FOREIGN PATENT DOCUMENTS

| 0 007 834 | 2/1980 | European Pat. Off. . |
| 0 199 407 | 10/1986 | European Pat. Off. . |
| 0 442 584 | 8/1991 | European Pat. Off. . |
| 2 370 718 | 6/1978 | France . |
| WO 94/00028 | 1/1994 | WIPO . |

OTHER PUBLICATIONS

Patent Abstracts of Japan, vol. 10, No. 144 (C-349) (2201), May 27, 1986, JP-61-1652, Jan. 7, 1986.

*Primary Examiner*—Shailendra Kumar
*Attorney, Agent, or Firm*—Oblon, Spivak, McClelland, Maier & Neustadt, P.C.

[57] ABSTRACT

L-amino acid amides are converted to the corresponding D-amino acid amides. An amide formed from an L-amino acid and an optically active (S)-α-alkylbenzylamine is subjected to dehydration condensation with an aryl aldehyde to form a Schiff's base, which is racemized at the amino acid moiety in the presence of a base to yield an N-allylidene-D-amino acid-(S)-amide. The less-soluble diastereomer N-allylidene-D-amino acid-(S)-amide is crystallized from the reaction mixture and recovered by means of solid/liquid separation. The N-allylidene form is readily hydrolyzed into the amino acid-(S)-amide and the starting aldehyde.

6 Claims, No Drawings

METHOD OF PREPARING D-AMINO ACID-N-(S)-α-ALKYLBENZYLAMIDE

BACKGROUND OF THE INVENTION

1. Field of the Invention

A process for stereocontrolled synthesis of D-amino acids.

2. Discussion of the Background

Among the D-amino acid-N-(S)-α-alkylbenzylamides represented by formula (1):

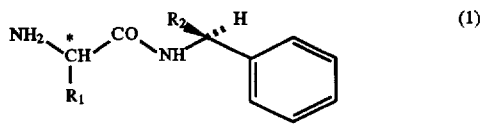

wherein the carbon atom indicated with a * has the D-amino acid structure, $R_1$ is an alkyl group having from 1 to 4 carbon atoms and $R_2$ is a methyl or ethyl group, those in which $R_1$ is a methyl, ethyl or isopropyl group and $R_2$ is a methyl or ethyl group are important substances which can be used as intermediates for substances having intense sweetness, as described in U.S. Pat. No. 5,286,509.

To prepare the D-amino acid-N-(S)-α-alkylbenzylamides described above, a method is generally employed wherein an N-protected D-amino acid whose amino group is protected with a benzyloxycarbonyl group or a t-butoxycarbonyl group and an optically active amine component are converted, using a condensation reagent such as N,N'-dicyclohexylcarbodiimide, to an intermediate N-protected D-amino acid-N-(S)-α-alkylbenzylamide, which is then deprotected to obtain the desired D-amino acid-N-(S)-α-alkylbenzylamide.

While the naturally occurring L-amino acids are manufactured industrially at a low cost on a large scale by means of fermentation, D-amino acids are obtained only by synthesizing DL-amino acids followed by optical resolution, because of the difficulty in producing them by fermentation. Accordingly, D-amino acids are far more expensive than L-amino acids. Therefore, D-amino acid-N-(S)-α-alkylbenzylamides, which are produced using such expensive D-amino acids, are still more expensive.

SUMMARY OF THE INVENTION

An objective of the present invention is to provide an industrial method for producing D-amino acid-N-(S)-α-alkylbenzylamides at a low cost without using expensive D-amino acids. This is accomplished by preparing an L- or DL-amino acid-N-(S)-α-alkylbenzylamide of formula (3):

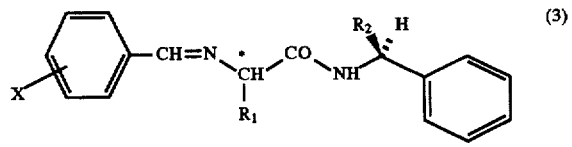

wherein the carbon atom indicated with a * has the L- or DL-amino acid structure, $R_1$ is an alkyl group having from 1 to 4 carbon atoms, $R_2$ is a methyl or ethyl group, X is hydrogen, halogen, nitro, cyano, hydroxyl, lower alkyl or lower alkoxy group, by dehydration condensation of an L- or DL-amino acid-N-(S)-α-alkylbenzylamide with an aryl aldehyde, then racemizing the amino acid moiety in a solvent containing a base which promotes racemization while crystallizing the N-(X-substituted phenylmethylidene)-D-amino acid-N-(S)-α-alkylbenzylamide, and recovering it by a solid/liquid separation procedure, and hydrolyzing it under acidic conditions to remove the aryl aldehyde.

DETAILED DESCRIPTION OF THE PREFERRED EMBODIMENTS

We have found that a Schiff's base (hereinafter referred generally to as N-allylidene-L-amino acid-(S)-amide) represented by formula (2):

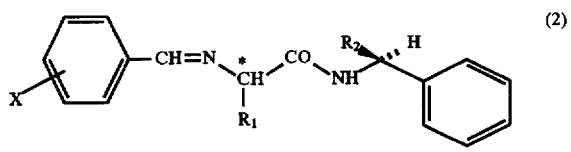

wherein the carbon atom indicated with a * has the L-amino acid structure, $R_1$ is an alkyl group having from 1 to 4 carbon atoms, $R_2$ is a methyl or ethyl group, X is hydrogen, halogen, nitro, cyano, hydroxyl, lower alkyl or lower alkoxy group, is readily racemized at the amino acid moiety in the presence of a base such as diazabicycloundecene (DBU) and sodium methoxide to yield the Schiff's base of the intended D-amino acid-N-(S)-α-alkylbenzylamide (hereinafter referred to generally as N-allylidene-D-amino acid-(S)-amide). The compound of formula (2) is obtained by reacting, as the starting material, an L-amino acid-N-(S)-α-alkylbenzylamide, which corresponds to a diastereomer of the intended D-amino acid-N-(S)-α-alkylbenzylamide, with an aryl aldehyde.

We have also found that N-allylidene-D-amino acid-(S)-amides can be crystallized selectively due to the difference in solubility between the two diastereomers resulting from the racemization reaction described above.

Furthermore, by combining these two characteristics, the N-allylidene-D-amino acid-(S)-amide can be exclusively crystallized while the racemization reaction is performed. The N-allylidene-D-amino acid-(S)-amide thus obtained can be hydrolyzed readily under acidic conditions into the original aryl aldehyde and the desired D-amino acid-N-(S)-α-alkylbenzylamide. We also found that even if a DL-amino acid is employed as the starting material, the corresponding N-allylidene-D-amino acid-(S)-amide can be crystallized exclusively. Japanese patent application No. 304783/1994 is incorporated herein by reference in its entirety.

Thus, the first aspect of the present invention is a method of preparing a D-amino acid-N-(S)-α-alkylbenzylamide represented by formula (1), wherein the N-(X-substituted phenylmethylidene)-L-amino acid-N-(S)-α-alkylbenzylamide represented by formula (2) is obtained by dehydration condensation of the corresponding L-amino acid-N-(S)-α-alkylbenzylamide with an aryl aldehyde. It is then racemized at the amino acid moiety in a solvent containing a base which promotes racemization, to produce the N-substituted phenylmethylidene-D-amino acid-N-(S)-α-alkylbenzylamide. Subsequently, the aryl aldehyde is removed by hydrolysis under acidic conditions.

(Formula 1)

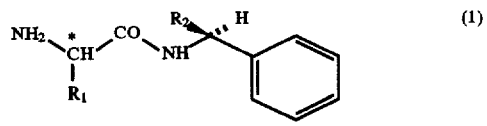

wherein the carbon atom indicated with a * has the D-amino acid structure, $R_1$ is an alkyl group having from 1 to 4 carbon atoms, and $R_2$ is a methyl or ethyl group.

(Formula 2)

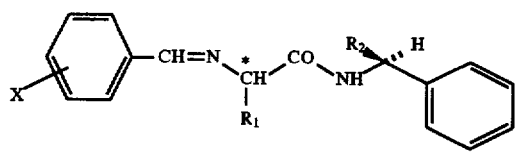

wherein the carbon atom indicated with a * has the L-amino acid structure, $R_1$ is an alkyl group having from 1 to 4 carbon atoms, $R_2$ is a methyl or ethyl group, X is hydrogen, halogen, nitro, cyano, hydroxyl, lower alkyl or lower alkoxy group.

The second aspect of the present invention is a method of preparing D-amino acid-N-(S)-α-alkylbenzylamides represented by formula (1) wherein an N-(X-substituted phenylmethylidene)-L- or DL-amino acid-N-(S)-α-alkylbenzylamide represented by formula (3) is obtained by dehydration condensation of the corresponding L- or DL-amino acid-N-(S)-α-alkylbenzylamide with an aryl aldehyde. The Schiff's base is racemized at the amino acid moiety in a solvent containing a base which promotes racemization while crystallizing the N-substituted phenylmethylidene-D-amino acid-N-(S)-α-alkylbenzylamide, which is obtained by a solid/liquid separation procedure and hydrolyzed under acidic conditions to remove the aryl aldehyde.

(Formula 3)

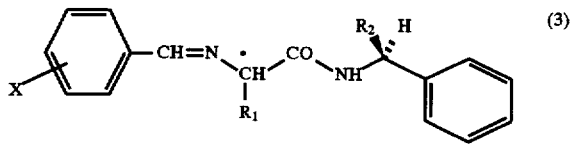

wherein the carbon atom indicated with a * has the L- or DL-amino acid structure, $R_1$ is an alkyl group having from 1 to 4 carbon atoms, $R_2$ is a methyl or ethyl group, X is hydrogen, halogen, nitro, cyano, hydroxyl, lower alkyl or lower alkoxy group.

The method according to the present invention is highly advantageous from an industrial point of view since it utilizes inexpensive L- or DL-amino acids instead of expensive D-amino acids as the starting materials to produce the corresponding D-amino acid-(S)-amides efficiently.

The aryl aldehyde employed in the present invention includes unsubstituted benzaldehyde or a benzaldehyde substituted with halogen, nitro, cyano, hydroxyl, lower alkyl or a lower alkoxy group. Although naphthylaldehyde may be employed for the Shiff's base moiety, an aryl aldehyde whose N-allylidene-amino acid-(S)-amide is readily crystallized is preferable when the two diastereomers of the N-allylidene-amino acid-(S)-amide are to be separated by crystallization from the racemate solution. Readily crystallizable arylaldehydes include benzaldehyde, p-chlorobenzaldehyde and p-anisaldehyde.

The L- or DL-amino acid-(S)-amides employed in the present invention include those with an amino acid side chain having from 1 to 4 carbon atoms, especially those with the α-alanine, α-aminobutyric acid or valine side chains.

Examples of optically active amines forming the amide moiety are (S)-α-methylbenzylamine and (S)-α-ethylbenzylamine.

To produce an N-allylidene-amino acid-(S)-amide, i.e., a Schiff's base, from an aryl aldehyde and an amino acid-(S)-amide described above, the reactants may be mixed in a suitable solvent or not, and the reaction is facilitated by removing water formed during the condensation process by distillation or by using a dehydrating agent.

The bases serving to racemize the N-allylidene-amino acid-(S)-amide include alkali metal hydroxides such as sodium hydroxide and potassium hydroxide, metal alkoxides such as sodium methoxide and potassium t-butoxide, and organic bases such as diazabicycloundecene (DBU) and diazabicyclononane (DBN).

While the amount of base is not particularly limited, the racemization reaction proceeds faster with a larger amount. Excessive amounts of base are not preferred from an economic point of view. Usually, the base is employed in an amount of 0.1–0.5 equivalent or more based on the N-allylidene-amino acid-(S)-amide.

The racemization proceeds satisfactorily at room temperature, although the reaction proceeds faster at higher temperatures. Usually, the racemization is conducted within a temperature range of from 0° to 100° C., preferably 20°–30° C.

The solvent used in the racemization reaction is preferably a solvent in which the N-allylidene-amino acid-(S)-amide and the base for the racemization are soluble. Examples of such solvents are alcohols such as methanol, ethanol and isopropanol, halogenated hydrocarbons such as dichloromethane and chloroform, esters such as ethyl acetate and butyl acetate, aromatic hydrocarbons such as benzene and toluene, ethers such as diethylether and tetrahydrofuran, nitriles such as acetonitrile, ketones such as acetone and methylethylketone, dimethylformamide and dimethylsulfoxide.

An acidic substance such as hydrochloric acid or sulfuric acid can be added to the reaction solution which has been subjected to the racemization reaction described above, establishing acidic conditions and decomposing the Schiff's base to yield the desired D-amino acid-(S)-amide and its diastereomer L-amino acid-(S)-amide.

Alternatively, by utilizing the difference in solubility between the two diastereomers, only the N-allylidene-D-amino acid-(S)-amide can be crystallized from the reaction solution which has been subjected to the racemization reaction. In such a case, standard crystallization methods can be employed such as concentrating the reaction solution, cooling the reaction solution, and adding a solvent which is miscible with the reaction solution but hardly dissolves the N-allylidene-D-amino acid-(S)-amide.

Furthermore, by combining the racemization reaction and the resolution crystallization of the diastereomers appropriately, the undesirable N-allylidene-L-amino acid-(S)-amide can be racemized into the intended N-allylidene-D-amino acid-(S)-amide while crystallizing the N-allylidene-D-amino acid-(S)-amide. By recycling the mother liquor of the resolution crystallization of the diastereomers in this procedure, the N-allylidene-L-amino acid-(S)-amide introduced as the starting material can be converted into the N-allylidene-D-amino acid-(S)-amide in very high yield. The present invention is further illustrated by the examples shown below.

In the pre-treatment of HPLC samples, the Schiff's base was treated with dilute hydrochloric acid to decompose it into the corresponding aryl aldehyde and amino acid-(S)-amide, and then the aryl aldehyde was removed by extraction with methylene chloride to obtain an aqueous layer containing the amino acid amides, which are diastereomers of each other, namely, D-amino acid-N-(S)-α-alkylbenzylamide and L-amino acid-N-(S)-α-alkylbenzylamide, which were subjected to the analysis. HPLC conditions: column: Inertsil ODS-2, 6Φ×150 mm, eluent: 0.1M $KH_2PO_4$(pH3.0)/MeCN=80/20(v/v), flow rate: 1 ml/min, temperature: room temperature. Detection: UV (210 m).

EXAMPLE 1

To 0.94 g (2.75 mmol) of N-p-chlorobenzylidene-α-DL-amino butyric acid-N-(S)-α-ethylbenzylamide, 5 ml of 0.5 mole/liter DBU/isopropanol solution was added and dissolved, and then 10 ml of water was added and the mixture was stirred at room temperature for 1 week. The crystallized slurry was separated by means of filtration with suction, and 1.02 g of crystals were obtained. These crystals were treated with dilute hydrochloric acid and subjected to HPLC, which revealed that 0.467 g (2.12 mmol) of α-D-amino butyric acid-N-(S)-α-ethylbenzylamide were contained. Yield: 77.1% (based on the starting DL form). α-L-amino butyric acid-N-(S)-α-ethylbenzylamide was contained only in an amount of 20 mg. The mother liquor was also analyzed in a similar manner and contained 33 mg (0.15 mmol) of α-D-amino butyric acid-N-(S)-α-ethylbenzylamide. Yield: 5.5% (based on the starting DL form).

EXAMPLE 2

To 0.866 g (2.53 mmol) of N-p-chlorobenzylidene-α-DL-aminobutyric acid-N-(S)-α-ethylbenzylamide, 4.6 ml of isopropanol were added. To this solution, 9.2 ml of 0.25N NaOH were added and the mixture was stirred at room temperature for 2 hours. A viscous oil which precipitated in the reaction mixture was separated by means of decantation to obtain 0.764 g. The oil was treated with dilute hydrochloric acid and subjected to HPLC, which revealed that 0.274 g (1.24 mmol) of α-D-amino butyric acid-N-(S)-α-ethylbenzylamide were contained. Yield: 49.0% (based on the starting DL form). α-L-amino butyric acid-N-(S)-α-ethylbenzylamide was contained only in an amount of 54 mg.

EXAMPLE 3

Except for using 0.611 g (1.98 mmol) of N-benzylidene-α-DL-amino butyric acid-N-(S)-α-ethylbenzylamide, the reaction was conducted in the same manner as Example 1. After stirring at room temperature for 2 weeks, the viscous oil obtained was separated by means of decantation to yield 0.609 g. HPLC analysis revealed that 0.289 g (1.31 mmols) of α-D-amino butyric acid-N-(S)-α-ethylbenzylamide were contained. Yield: 66.2% (based on the starting DL form). α-L-amino butyric acid-N-(S)-α-ethylbenzylamide was contained only in the amount of 45 mg.

EXAMPLE 4

Except for using 0.7 g (2.17 mmols) of N-p-methyl-benzylidene-α-DL-amino butyric acid-N-(S)-α-ethylbenzylamide, the reaction was conducted in the same manner as Example 1. After stirring at room temperature for 2 weeks, the viscous oil obtained was separated by means of decantation to yield 0.671 g. HPLC analysis revealed that 0.249 g (1.31 mmol) of α-D-amino butyric acid-N-(S)-α-ethylbenzylamide were contained. Yield: α-L-amino butyric 52.1% (based on the starting DL form) acid-N-(S)-α-ethylbenzylamide was contained only in an amount of 54 mg.

EXAMPLE 5

0.29 g (0.89 mmol) of N-p-chlorobenzylidene-α-DL-amino butyric acid-N-(S)-α-methylbenzylamide was dissolved in 2.5 ml of 0.5M/L DBU/isopropanol solution and the mixture was stirred at room temperature while adding 2 ml of water in aliquots. Subsequently, the mixture was stirred at room temperature overnight, and the precipitated crystals were separated by means of filtration with suction to obtain 0.478 g crystals. HPLC analysis after the treatment with dilute hydrochloric acid revealed that the crystals contained 0.14 g (0.686 mmol) of α-D-aminobutyric acid-N-(S)-α-methylbenzylamide. Yield: 77.1% (based on the starting DL form). α-L-aminobutyric acid-N-(S)-α-methylbenzylamide was contained only in a trace amount.

EXAMPLE 6

0.51 g (1.43 mmol) of N-p-chlorobenzylidene-L-valine-N-(S)-α-ethylbenzylamide was dissolved in 30 ml of isopropanol and 41 mg of sodium methoxide was added and the reaction mixture was stirred for 1.5 hours while being heated at 60° C. A 1 ml aliquot of the reaction mixture was taken and treated with dilute hydrochloric acid and subjected to HPLC, which revealed that L-valine-N-(S)-α-ethylbenzylamide and D-valine-N-(S)-α-ethylbenzylamide were present in almost equal amounts. The remainder of the reaction mixture was evaporated under reduced pressure to remove the solvent and the residue was taken up with 10 ml of hexane. After storage in a refrigerator overnight, the precipitated crystals were separated by means of filtration with suction to obtain 0.407 g (as dried) of the crystals. HPLC analysis following treatment with dilute hydrochloric acid revealed that the crystal contained 0.201 g (0.859 mmol) of D-valine-N-(S)-α-ethylbenzylamide. Yield: 60.1% (based on the starting L form). L-valine-N-(S)-α-ethylbenzylamide was contained only in an amount of 7.2 mg.

EXAMPLE 7

0.168 g (0.50 mmol) of N-p-methylbenzylidene-L-valine-N-(S)-α-ethylbenzylamide was dissolved in 10 ml of isopropanol. Sodium methoxide (81 mg) was added and the reaction mixture was stirred for 5 hours while being heated at 60° C. An aliquot of the reaction mixture was taken and treated with dilute hydrochloric acid and subjected to HPLC, which revealed that L-valine-N-(S)-α-ethylbenzylamide and D-valine-N-(S)-α-ethylbenzylamide were present in almost equal amounts. The remainder of the reaction mixture was admixed with 15 ml of water and stored in a refrigerator overnight, and then the precipitated crystals were separated by means of filtration with suction to obtain 67.6 mg of the crystals. HPLC analysis following the treatment with dilute hydrochloric acid revealed that the crystals contained 39 mg (0.167 mmol) of D-valine-N-(S)-α-ethylbenzylamide. Yield: 33.4% (based on starting L form). L-valine-N-(S)-α-ethylbenzylamide was contained only in an amount of 2 mg.

EXAMPLE 8

Except for using 0.70 g (2.0 mmol) of N-m-methylbenzylidene-L-valine-N-(S)-α-ethylbenzylamide, the reaction was conducted in the same manner as Example 1. The analysis of the crystals obtained revealed that 0.14 g (0.60 mmol) of D-valine-N-(S)-α-ethylbenzylamide was contained. Yield: 30.2% (based on the starting form). L-valine-N-(S)-α-ethylbenzylamide was contained only in an amount of 75 mg.

According to the inventive method, D-amino acid-(S)-α-alkylbenzylamides can be produced from L- or DL-amino acids as the starting materials, which are inexpensive and available in large amounts, instead of D-amino acids which are expensive and are not readily available.

Obviously, numerous modifications of the present invention are possible in light of the above teaching. It is, therefore, to be understood that within the scope of the appended cliams, the invention may be practiced otherwise than as specifically described herein.

We claim:

1. A method of preparing a D-amino acid-N-(S)-α-alkylbenzylamide of formula (1):

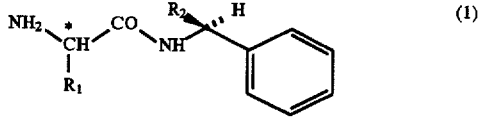

wherein the carbon atom indicated with a * has the D-amino acid structure, R₁ is an alkyl group having from 1 to 4 carbon atoms and R₂ is a methyl or ethyl group, comprising:
preparing an N-(X-substituted phenylmethylidene)-L-amino acid-N-(S)-α-alkylbenzylamide of formula (2):

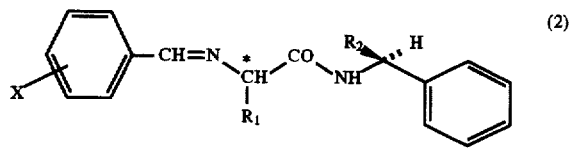

wherein the carbon atom indicated with a * has the L-amino acid structure, R₁ is an alkyl group having from 1 to 4 carbon atoms, R₂ is a methyl or ethyl group, X is hydrogen, halogen, nitro, cyano, hydroxyl, lower alkyl or lower alkoxy group, by dehydration condensation of an L-amino acid-N-(S)-α-alkylbenzylamide with an aryl aldehyde, racemizing the amino acid moiety in a solvent containing a base which promotes racemization to produce an N-(X-substituted phenylmethylidene)-D-amino acid-N-(S)-α-alkylbenzylamide, and removing the aryl aldehyde by hydrolysis under acidic conditions.

2. A method of preparing a D-amino acid-N-(S)-α-alkylbenzylamide of formula (1):

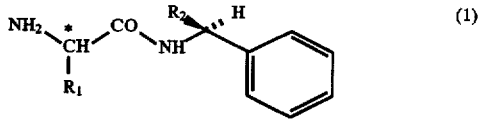

wherein the carbon atom indicated with a * has the D-amino acid structure, R₁ is an alkyl group having from 1 to 4 carbon atoms and R₂ is a methyl or ethyl group, comprising:
preparing a N-(X-substituted phenylmethylidene)-L- or DL-amino acid-N-(S)-α-alkylbenzylamide of formula (3):

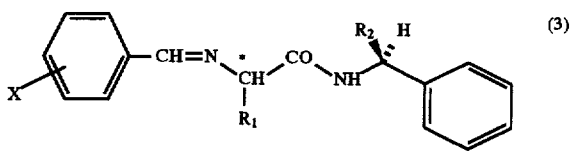

wherein the carbon atom indicated with a * has the L- or DL-amino acid structure, R₁ is an alkyl group having from 1 to 4 carbon atoms, R₂ is a methyl or ethyl group, X is hydrogen, halogen, nitro, cyano, hydroxyl, lower alkyl or lower alkoxy group, by dehydration condensation of an L- or DL-amino acid-N-(S)-α-alkylbenzylamide with an aryl aldehyde, racemizing the amino acid moiety in a solvent containing a base which promotes racemization while crystallizing an N-(X-substituted phenylmethylidene)-D-amino acid-N-(S)-α-alkylbenzylamide, and recovering said N-(X-substituted phenylmethylidene)-D-amino acid-N-(S)-α-alkylbenzylamide by a solid/liquid separation procedure and hydrolyzing it under acidic conditions to remove the aryl aldehyde.

3. The method of claim 1 wherein the racemization promoting base employed is a metal alkoxide, alkaline metal hydroxide or organic base.

4. The method of claim 2 wherein the racemization promoting base employed is a metal alkoxide, alkaline metal hydroxide or organic base.

5. The method of claim 1 wherein the L-amino acid-N-(S)-α-alkylbenzylamide employed is α-aminobutyric acid-N-(S)-α-methylbenzylamide, α-aminobutyric acid-N-(S)-α-ethylbenzylamide, valine-N-(S)-α-methylbenzylamide or valine-N-(S)-α-ethylbenzylamide.

6. The method of claim 2 wherein the DL-amino acid-N-(S)-α-alkylbenzylamide employed is α-aminobutyric acid-N-(S)-α-methylbenzylamide, α-aminobutyric acid-N-(S)-α-ethylbenzylamide, valine-N-(S)-α-methylbenzylamide or valine-N-(S)-α-ethylbenzylamide.

* * * * *